United States Patent [19]

Furse

[11] Patent Number: 5,354,483
[45] Date of Patent: Oct. 11, 1994

[54] DOUBLE-ENDED TUBE FOR SEPARATING PHASES OF BLOOD

[75] Inventor: Martin L. Furse, Vancouver, Canada

[73] Assignee: Andronic Technologies, Inc., Mississauga, Canada

[21] Appl. No.: 955,341

[22] Filed: Oct. 1, 1992

[51] Int. Cl.$^5$ .............................................. B01D 21/26
[52] U.S. Cl. .................... 210/789; 210/137; 210/516
[58] Field of Search ............... 210/516, 136, 137, 359, 210/789

[56] References Cited

U.S. PATENT DOCUMENTS

| | | |
|---|---|---|
| 3,120,490 | 2/1964 | Samson ................... 210/DIG. 13 X |
| 3,456,647 | 7/1969 | Wada . |
| 3,508,653 | 4/1970 | Coleman . |
| 3,741,400 | 6/1973 | Dick . |
| 3,849,072 | 11/1974 | Ayres . |
| 3,852,194 | 12/1974 | Zine, Jr. . |
| 3,887,466 | 6/1975 | Ayres . |
| 3,894,952 | 7/1975 | Ayres ................................ 210/516 |
| 3,929,646 | 12/1975 | Adler . |
| 3,932,277 | 1/1976 | McDermott et al. . |
| 3,941,699 | 3/1976 | Ayres . |
| 3,957,654 | 5/1976 | Ayres ................................ 210/516 |
| 4,000,829 | 1/1977 | Johnson, Jr. et al. . |
| 4,001,122 | 1/1977 | Griffin . |
| 4,021,352 | 5/1977 | Sarstedt . |
| 4,046,699 | 9/1977 | Zine, Jr. . |
| 4,083,784 | 4/1978 | Zine, Jr. . |
| 4,104,127 | 8/1978 | Bucalo . |
| 4,142,668 | 3/1979 | Lee ................................ 210/576 X |
| 4,152,270 | 5/1979 | Cornell . |
| 4,154,690 | 5/1979 | Ballies . |
| 4,169,060 | 9/1979 | Columbus ........................... 210/516 |
| 4,189,382 | 2/1980 | Zine, Jr. . |
| 4,192,438 | 3/1980 | Foster et al. . |
| 4,202,769 | 5/1980 | Greenspan . |

(List continued on next page.)

FOREIGN PATENT DOCUMENTS

| | | |
|---|---|---|
| 0100664 | 2/1984 | European Pat. Off. . |
| 0098150 | 12/1984 | European Pat. Off. . |
| 0285076 | 10/1988 | European Pat. Off. . |
| 0341586 | 11/1989 | European Pat. Off. . |
| 0341587 | 11/1989 | European Pat. Off. . |
| 0348116 | 12/1989 | European Pat. Off. . |
| 1806196 | 7/1969 | Fed. Rep. of Germany . |

OTHER PUBLICATIONS

*An Automated Device for Aseptically Aspirating Serum From Blood Collection Tissues*, IEEE Transactions on Biomedical Engineering, vol. BME 36, No. 6, Jun. 1986.
*Idea Caps Risks in Lab*, The London Sunday Times, Jan. 24, 1988.

Primary Examiner—Frank Spear
Attorney, Agent, or Firm—Klarquist Sparkman Campbell Leigh & Whinston

[57] ABSTRACT

A method of partitioning a pre-selected phase of a sample of liquid having a plurality of phases of differing densities, a separating element and a tube containing the separating element. The sample of liquid is placed in a first chamber of a tube that is separated from a second chamber by a separating element. The separating element slidably engages the interior surface of the tube in a substantially fluid-tight manner. A fluid passage is disposed through the separating element and includes an initially closed fluid passage. The phases are ordered by axial centrifugation wherein the tube is rotated about its longitudinal axis, the separating element is moved within the tube reducing the volume of the first chamber, a pre-selected phase of the liquid is forced from the first chamber through the fluid passage into a second chamber. The reduction of the volume of the first chamber is controlled using phase-separation information. The separator may also include a filter for filtering the fluid. The method is useful in the separation of blood components.

5 Claims, 5 Drawing Sheets

U.S. PATENT DOCUMENTS

| | | |
|---|---|---|
| 4,279,863 | 7/1981 | Friehler .......................... 210/927 X |
| 4,294,707 | 10/1981 | Ikeda et al. . |
| 4,326,959 | 4/1982 | Ferrara . |
| 4,350,593 | 10/1982 | Kessler . |
| 4,369,117 | 1/1983 | White . |
| 4,417,981 | 11/1983 | Nugent . |
| 4,425,235 | 1/1984 | Cornell et al. ...................... 210/516 |
| 4,443,345 | 4/1984 | Wells . |
| 4,464,254 | 8/1984 | Dojki et al. . |
| 4,492,634 | 1/1985 | Villa-Real . |
| 4,522,713 | 6/1985 | Nussbaumer et al. . |
| 4,535,918 | 8/1985 | Heiligman et al. . |
| 4,602,995 | 7/1986 | Cassaday et al. . |
| 4,630,753 | 12/1986 | Anscherlik . |
| 4,639,316 | 1/1987 | Eldegheidy . |
| 4,811,866 | 3/1989 | Golias . |
| 4,828,716 | 5/1989 | McEwen et al. . |
| 4,976,925 | 12/1990 | Porcher et al. . |
| 5,019,243 | 5/1991 | McEwen et al. . |
| 5,030,341 | 7/1991 | McEwen et al. . |
| 5,065,907 | 11/1991 | Allen . |
| 5,078,970 | 1/1992 | Teodorescu et al. . |

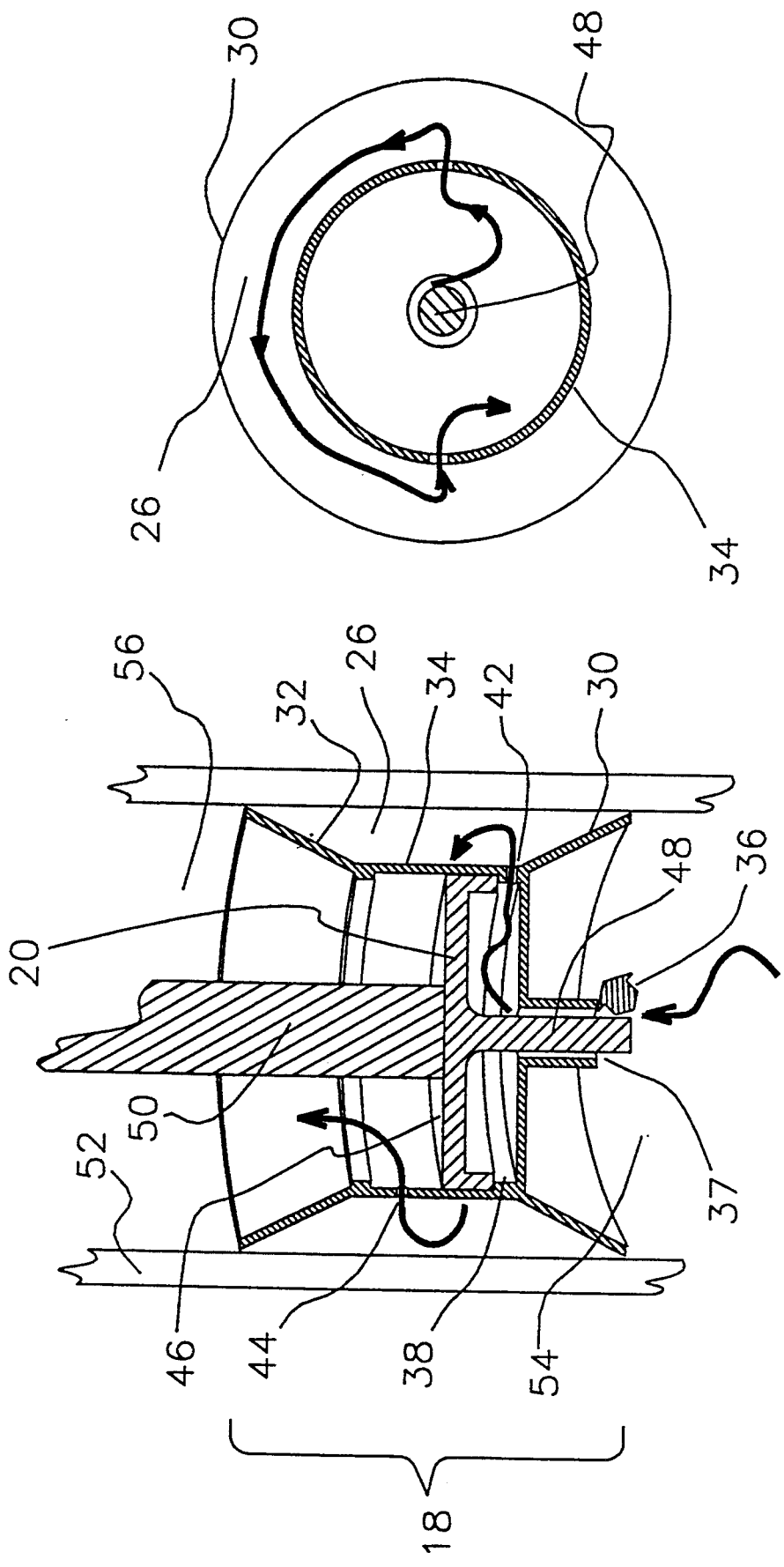

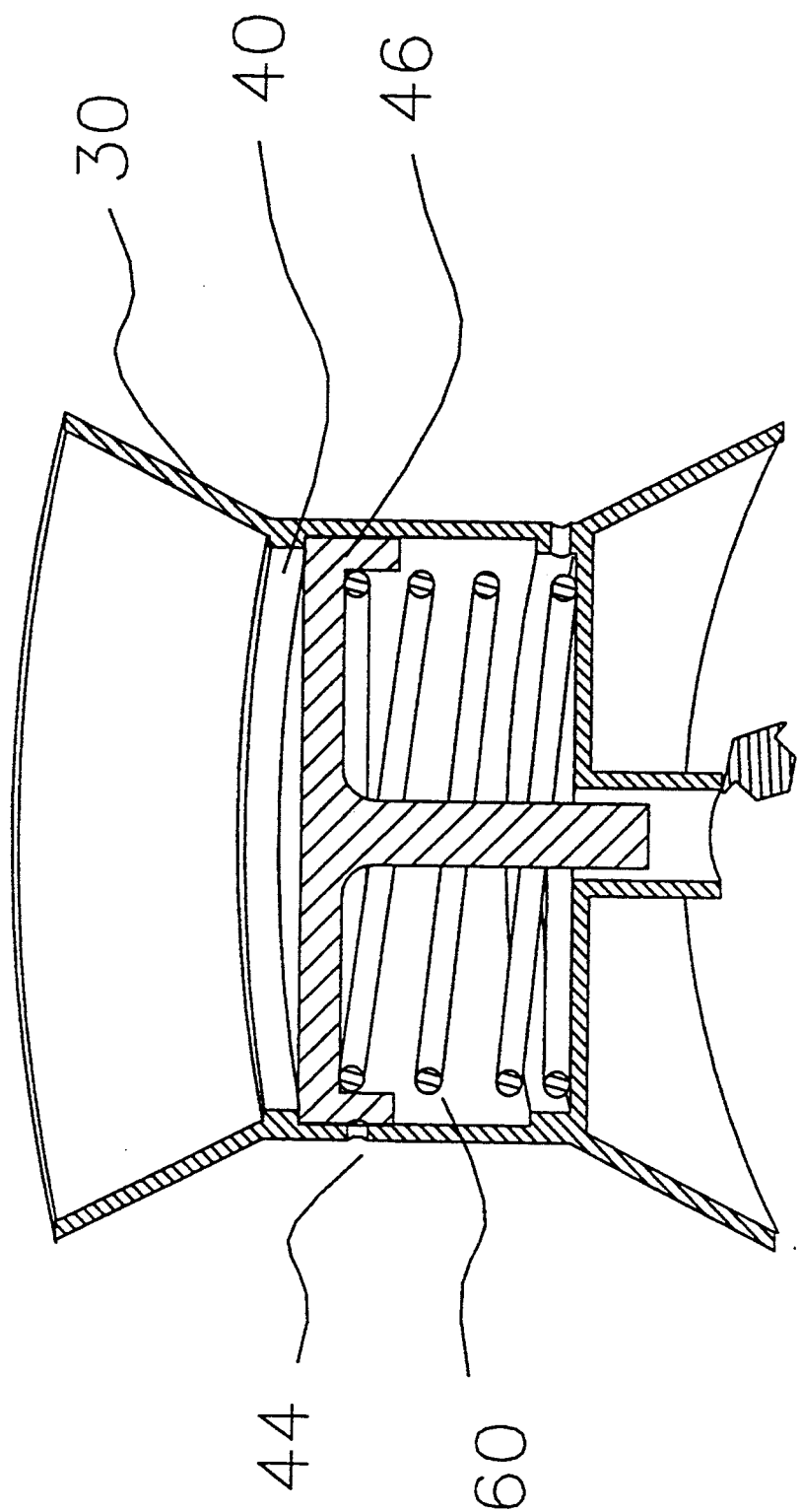

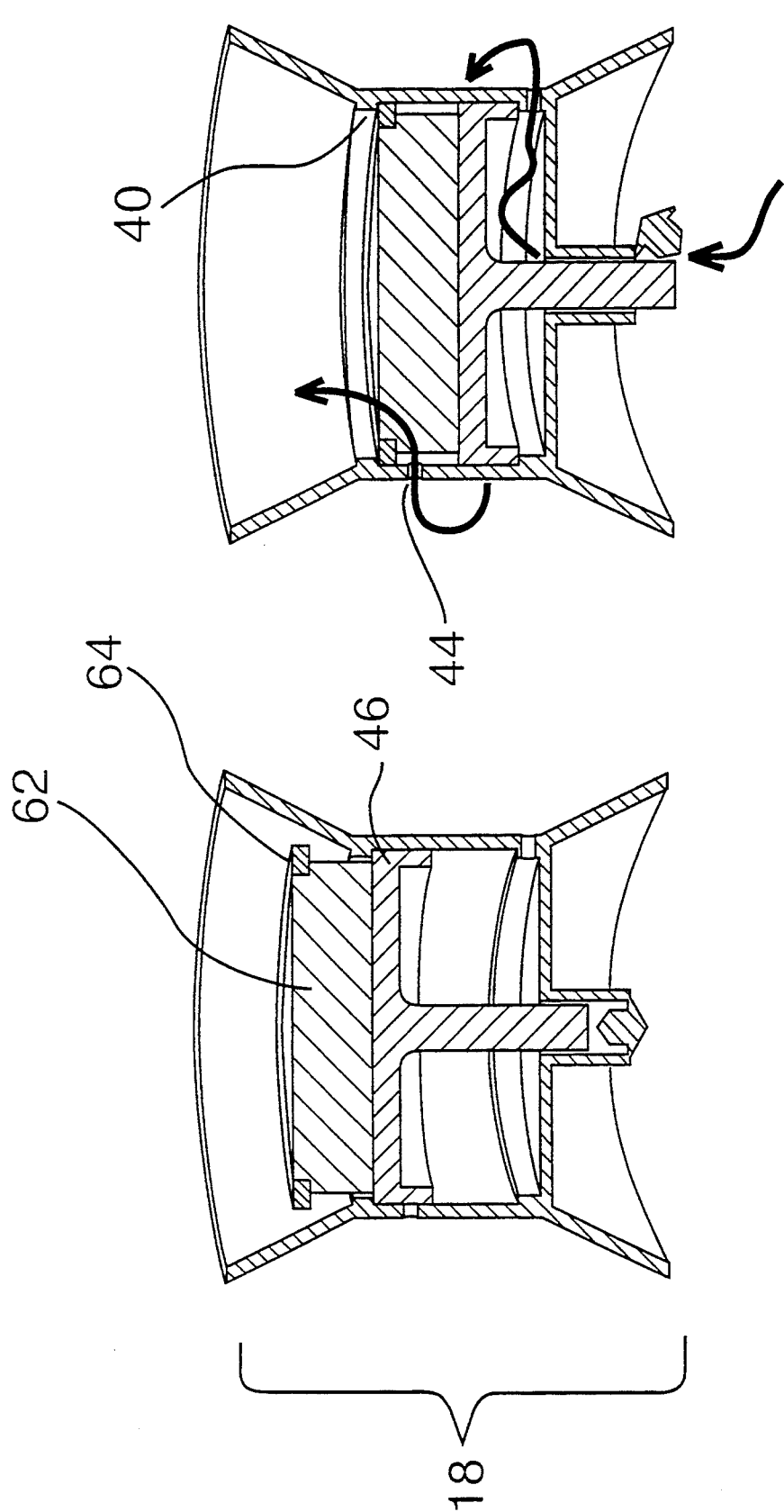

DOUBLE-ENDED TUBE FOR SEPARATING PHASES OF BLOOD

FIELD OF THE INVENTION

The present invention refers to a method and apparatus for separating a pre-selected phase of a sample of liquid such as blood contained in a chamber, and pertains to means for ordering the phases of a sample of liquid contained in a chamber by rotating the chamber about its longitudinal axis. In particular, the invention pertains to apparatus for collecting a blood sample in a tubular chamber, separating the phases of the blood sample by rotating the tubular chamber about its longitudinal axis, and receiving from the chamber the separated phases in order of phase. Particularly, the invention pertains to a blood collection tube having ends separated by a separating element where a first end receives a sample of blood and a pre-selected phase of the blood may be received from the other end.

BACKGROUND OF THE INVENTION

Blood to be analyzed for diagnostic and monitoring purposes is customarily collected by venipuncture through a special cannula or needle attached to a syringe or evacuated collection tube. Such collection techniques and devices must offer ease and flexibility of use because of the large number of blood specimens that are processed and because of requirements for additives, variable volumes and adaptation to individual medical conditions.

Separation of the constituent phases, serum or plasma from the cells, is often necessary for laboratory analysis and is usually carried out by centrifugation or, occasionally, by filtration. This separation may require fractionation of minor as well as major components. Once separated the phases are best kept in an inert container, physically and chemically isolated, to avoid disturbance of analyte concentrations. It may be necessary to store them under controlled environmental conditions of temperature, atmosphere or light.

Thus there is a need for a blood collection and separation device or system which combines the features of: ability to separate the blood phases under conditions which limit personnel exposure; maintenance of these phases separated and unchanged; monitoring of gross characteristics of the phases; ready adaptability to varying blood collection requirements; and flexibility for stand-alone use or integration into automated systems.

Serum and plasma are commonly used analytical samples. If serum is desired the specimen must be permitted to clot or coagulate before further separation is attempted. Activation of this clot formation may result as a consequence of contact with the glass collection tube in which the blood was collected and can be enhanced by the addition of various clot-activating materials as described in U.S. Pat. No. 4,189,382 by Zine. If plasma is desired the specimen must have an anticoagulant mixed with it immediately after collection. For this purpose such anticoagulant materials are commonly placed in blood collection devices at the time of manufacture.

The most commonly used blood collection devices are evacuated tubes. They are characterized by advantages and disadvantages in certain situations. The pre-evacuated blood collection tube (such as described by Kleiner U.S. Pat. No. 2,460,641) has the following advantages: once sterilized, its interior remains sterile without additional packaging; simplicity of structure and use, in that its basic form consists of only a glass tube permanently closed at one end with a rubber stopper in the open end; and it is self-sealing when blood drawing is complete and the cannula which was used to puncture the rubber stopper has been removed.

The blood plasma or serum phase is readily separated from the blood cells or clot phase by centrifugation since the specific gravities of these two phases are different. The recommended and usual practice is to centrifuge the specimen at a relative centripetal acceleration of 1000 to 1200 gravities for about 10 minutes. Various materials and devices have been described to physically separate the serum or plasma from the cellular phase, which are either activated during centrifugation or applied after separation is complete. These include gel-like compositions with densities intermediate to the phases as described, for example, in U.S. Pat. No. 4,350,593 by Kessler and U.S. Pat. No. 3,852,194 and U.S. Pat. No. 4,083,784 by Zine. Such substances, as commonly used, are sealed in the evacuated blood collection tube at the time of manufacture and will migrate to, and form a barrier at, the interface between the blood phases under the influence of the correct centrifugal force. A problem with such materials is that although they are made from substances with low chemical reactivity they nevertheless contain substances which will contaminate the serum or plasma (such as low levels of some metals used as catalysts for the formation of those compositions). Some substances which are determined by blood analysis (such as low concentrations of organic-soluble, hydrophobic drugs) can be significantly adsorbed or absorbed out of the sample by such gel-like materials, resulting in incorrect analyses. Other separators consisting of a variety of plug-like objects have been used as described, for example, in U.S. Pat. No. 4,492,634 by Villa-Real, U.S. Pat. No. 3,508,653 by Coleman, U.S. Pat. No. 4,417,981 by Nugent, U.S. Pat. No. 4,425,235 by Cornell, and U.S. Pat. No. 4,369,117 by White. Unfortunately, these devices are more expensive to make and insert into the pre-evacuated collection tube and the barriers they provide are no more reliable or effective than the simpler, less expensive gel-like separation materials.

Irrespective of the relative expense of plug-like barrier devices, the main problem with such barriers of the prior art is that during blood collection it is impossible to keep blood from getting between the tube closure and the barrier device. Coleman, U.S. Pat. No. 3,508,653 describes a plug-like barrier which is removably attached to the stopper, but does not demonstrate how blood is prevented from being interposed between the stopper and plug-like barrier. In fact, he states that the plug need not be attached to the stopper, but only restrained from moving prior to centrifugation. Since Coleman's barrier must allow passage of fluid around it when pressure is applied, it follows that the space between the barrier and stopper, along with the rest of the tube, is evacuated prior to blood collection. If the space between the stopper and barrier is evacuated, then blood may forcibly fill the space between the two parts. This is entirely unacceptable because there is no certain way of isolating the cellular blood component of the blood located between the barrier and the stopper from the separated serum or plasma thus negating the effect of the barrier. Both Nugent U.S. Pat. No. 4,417,981 and Adler U.S. Pat. No. 3,929,646 try to address this problem by providing a path for the whole blood to move around and past the plug-like barrier during sample collection or centrifugation. However, in practice once blood interposed between the stopper and barrier has clotted, these passages are insufficient to ensure that the cellular component of the interposed blood will migrate to the other side of the barrier during centrifugation. Both Nugent and Cornell U.S. Pat. No. 4,425,235 try to address this problem by including a migrating gel in their plug-like barriers, but this negates the benefits of solid barriers over gel barriers. White, Pat. No. 4,369,117, avoids the problem by inserting his plug-like barrier into the collection tube after blood collection has occurred. This is not desirable because an additional, hazardous step is required in handling an open tube.

An additional problem with many barriers is incomplete isolation of the serum or plasma from the cellular phase. In the case of gel-like barriers, severe jarring as might occur if the sample is shipped or mailed to a testing laboratory, may disrupt the seal provided by the barrier. If the isolation provided by the barrier is incomplete or disrupted, interaction of the separated phases will cause inaccurate analytical results. Moreover, prolonged contact of the blood phases with a gel-like barrier separator will increase the degree of analytical error caused by interaction between the blood and the barrier. Therefore, with most such devices it is necessary to separate the phases soon after the blood is collected and then transfer the separated plasma or serum to another container for prolonged storage or transport. Problems which then arise are that the transferred sample can become incorrectly identified and that the process of transfer exposes the user to potentially hazardous or infectious blood.

A portion of the serum or plasma may be completely isolated after centrifugation by a device which is inserted into the open end of the collection tube and permits the one-way flow of serum from the collection tube into a separate sampling container through a filter which prevents any of the fibrin from passing into the serum or plasma sample. Fibrin in blood serum can cause blood analysis machines to clog; therefore, many clinical chemistry laboratories filter all serum as a precaution. Such filtering devices are described, for example, in U.S. Pat. No. 4,464,254 by Dojki, U.S. Pat. No. 3,929,646 by Adler, U.S. Pat. No. 4,602,995 by Cassaday and are manufactured and distributed under the name of "serum/plasma filter" by W. Sarstedt, Inc. It is possible to isolate the phases of blood with such a device so as to prevent diffusion of ions or other interaction between the phases. However, their use requires additional manipulation of the collection tube, consequent exposure of the user to the blood specimen and risk of contamination of the sample. Related devices employ multiple flexible containers with provision for flow of blood fractions from the collecting blood bag into a separate reservoir (for example, U.S. Pat. No. 4,447,220 by Eberle and U.S. Pat. No. 4,322,298 by Persidsky) but these are bulky complex systems only for the separation of anticoagulated blood and are not suitable for collection and preparation of samples for routine clinical analysis.

In some situations the use of conventional centrifuges to separate serum or plasma from the cellular component of blood specimens is undesirable because it requires a large and expensive centrifuge, best suited for separating batches of several specimens simultaneously. This operation is inefficient when the serial analyses of single samples is urgently required. Time must also be taken to properly balance the centrifuge rotor to prevent excessive vibration which may damage the machine and specimens. An apparatus such as the "Stat-Spin" axial centrifuge, developed and manufactured by Norfolk Scientific, Inc. (Norwood, Mass.), can effect this separation on a single specimen more quickly, however, the technique employed by this apparatus is limited to anticoagulated blood, collected separately in a conventional blood collection device and transferred to a specialized centrifuge chamber containing gel-like separation material. Moreover this transfer increases the hazard of contamination or loss of the sample, misidentification, and exposure of the operator to potentially infectious material in the blood. The use of an additional container increases the cost of analyzing a sample.

Similar objections and disadvantages apply to the "ACR-90" centrifuge chamber, rotor and "Airfuge" drive manufactured and sold by Spinco Division of Beckman Instruments, Inc. (Palo Alto, Calif.). This rotor is dual chambered and intended for isolation of the large lipid particles from lipemic sera. At high rotational speeds (typically greater than 90,000 rpm) the plastic chamber deforms, permitting the less dense lipid phase to migrate to a second chamber where it is trapped. Other axially spun centrifuge rotors, with a single volume often divided by vanes, are well known as "zonal rotors" and used for harvesting particles from a large volume (0.3–1.7 liters) of dilute solution such as preparations for vaccine by virologists and other such macromolecular isolates (Anderson, N. G.: Preparative zonal centrifugation. Methods of Biochemical Analysis 1967; 15: 271–310). Zonal rotors may be loaded and unloaded through a rotating seal while spinning (dynamically). A majority cannot be loaded or unloaded statically, while a few cannot be loaded or unloaded dynamically. In either case they are usually used for ultracentrifugation at rotational speeds of 20,000–60,000 rpm. Fluids are loaded by a pump and unloaded from them by displacement with air or a denser fluid pumped in during rotation. A single chamber, axially spun, centrifuge rotor with a variable volume which can be used for separation of plasma from blood was described by Brown in U.S. Pat. No. 4,530,691. This is intended for preparation of blood fractions for therapeutic use and relies upon the fractionation by centrifugation and isolation of those fractions by release of pressure exerted by a spring-loaded movable mandrel upon a flexible chamber. In this way the higher density cellular components can be taken off from the outer radius and the plasma through the center through fluid conduits while the rotor is in motion. Neither of these technologies (zonal ultracentrifugation nor centrifuge with a movable mandrel) is suitable for the fractionation of blood specimens as normally required for clinical analyses. The volumes are too large; they require the use of anticoagulants and cannot be used with clotted whole blood; and they are not readily adapted for automated procedures.

Procedures for blood separation and analysis expose laboratory personnel to infectious agents that may be passed through contact with blood; e.g. hepatitis or acquired immune deficiency syndrome. In addition, conventional batch processing of blood specimen separation is labor-intensive and has not generally been automated whereas other processes in clinical laboratories have. Automation of blood separation can effectively isolate laboratory personnel from the dangers of blood processing while theoretically increasing the speed of the overall analytical procedure.

U.S. Pat. Nos. 4,828,716, 5,019,243, and 5,030,341 by McEwen et al. describe a method of separating a sample of blood contained in a tubular chamber wherein the tubular chamber and its contents are rotated about the chamber's longitudinal axis and providing a means of processing a sample of blood having the features of: ability to separate the blood phases under conditions which limit personnel exposure; maintenance of these phases separated and unchanged; monitoring of gross characteristics of the phases; ready adaptability to varying blood collection requirements; and flexibility for stand-alone use or integration into automated systems. The present invention provides an improved blood collection and separation device according to the invention of McEwen et al as described in U.S. Pat. Nos. 4,828,716, 5,019,243, and 5,030,341.

SUMMARY OF THE INVENTION

The present invention provides a method of partitioning a pre-selected phase of a sample of liquid having a plurality of phases of different densities, comprising the steps of:

(a) Introducing a sample of liquid through a first end of a tube and into a first chamber within the tube wherein the first chamber is separated from a second chamber at a second end of the tube by a separating element. The separating element slidably engages the interior surface of the tube wall in an essentially fluid-tight manner and has a flow-restriction orifice therein to permit fluid flow between the first and second chambers when influenced by a force.

(b) Ordering the phases of the liquid within the tube using axial centrifugation.

(c) While the phases are ordered, reducing the volume of the first chamber so as to cause one phase of the liquid to flow through the flow-restriction orifice. The phase that is then in the second chamber may be removed through the second end of the tube.

The flow-restriction orifice permits fluid flow while the volume of the first chamber is being reduced, but restricts flow at other times.

Initially the second chamber may be an incipient chamber that forms as the separating element is moved within the tube.

The method allows fluid to flow through a passage so that it can be monitored external to the tube.

The method also allows that the liquid that is being separated is serum or plasma.

The method also allows that the method employs centrifugal force to effect separation.

A tube for partitioning and separating a sample of liquid having a plurality of phases of different densities is also disclosed. The tube has a separating element located within the tube that separates the tube into two chambers. The separating element slidably engages the interior surface of the tube wall in an essentially fluid-tight manner and has a passage for fluid flow between the chambers. The passage is initially closed to prevent premature fluid flow. The tube has sealable openings at both ends.

The passage through the separating element has a flow-restriction orifice for restricting the flow of liquid. The flow restriction may also be a valve. The passage may also include a convoluted path.

The separating element may include a filter means for filtering liquid that passes through the passage.

The passage may comprise a space formed between the separating element and the interior wall of the tube.

DESCRIPTION OF THE DRAWINGS

The invention is described with reference to the following drawings:

FIG. 3 shows a cross-section of the separating element showing its configuration during use when separating a sample of liquid and shows, by arrows, the general direction of fluid flow.

FIG. 4 shows a cross-section of the preferred embodiment of the separating element and including a spring which causes a substantially impermeable post-separation fluid seal.

FIG. 5 shows a cross-section of the prefered embodiment of the separating element which includes a filter.

DETAILED DESCRIPTION

Figure 1:
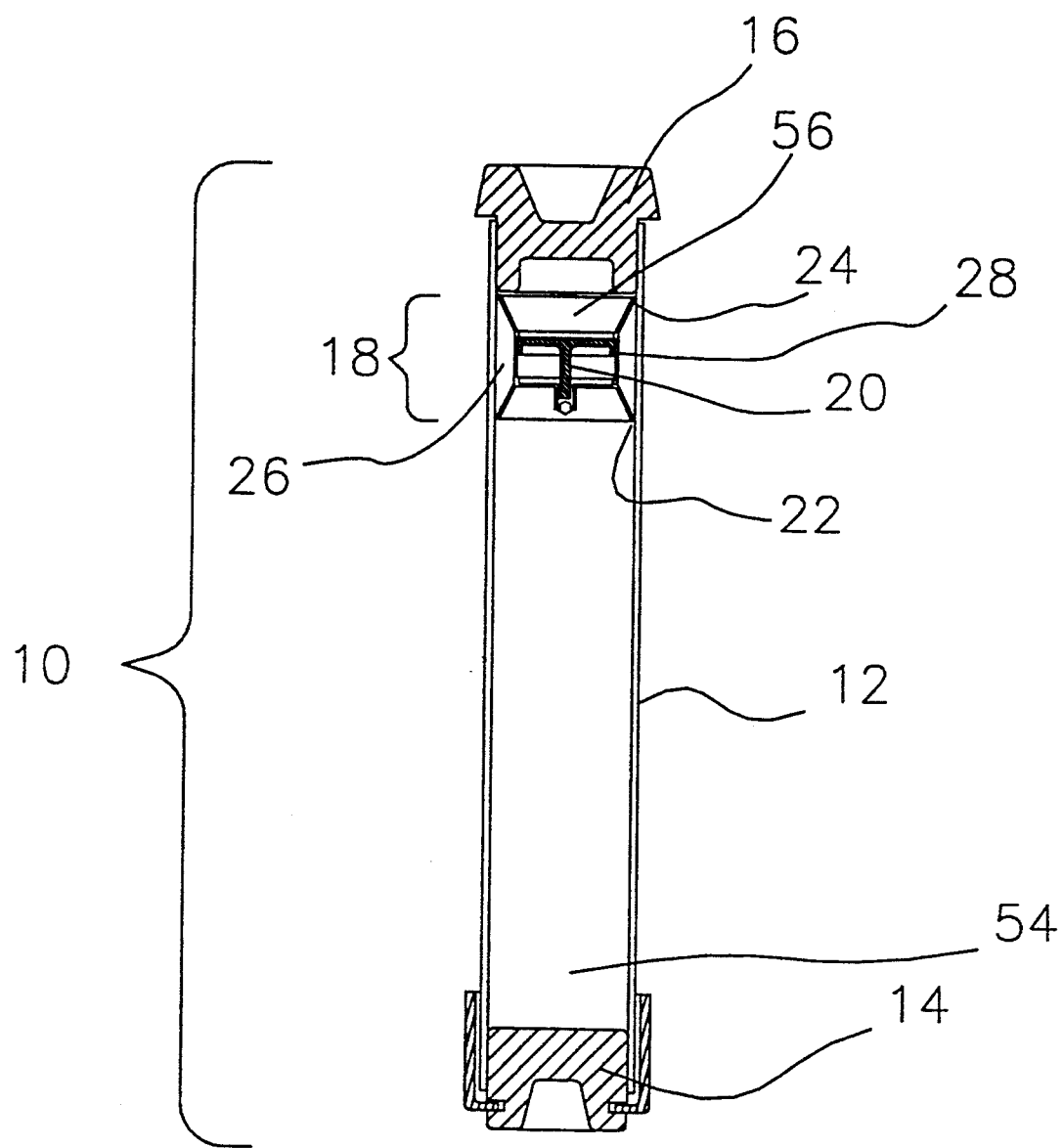
FIG. 1 shows a cross-section of the preferred embodiment of the present invention showing a double-ended blood collection tube in which is located a separating element.

Referring to FIG. 1, blood tube 10 consists of cylindrical tube 12, first closure 14, second closure 16, and separating element 18. Cylindrical tube 12 is sealed at a first end by first closure 14 thereby creating a vessel capable of containing a liquid. A second and opposing end of cylindrical tube 12 is sealed by second closure 16. Positioned within the cylindrical tube 12 and between first closure 14 and second closure 16 is separating element 18. The location of separating element 18 between first closure 14 and second closure 16 divides the space within blood tube 10 into two chambers: first chamber 54 and second chamber 56. Second chamber 56 may be an incipient chamber which becomes second chamber 56 as separating element 18 is moved within cylindrical tube 12. Separating element 18 is slidably located within the tube and has first wiping seal 22 and second wiping seal 24 engaging the interior wall of cylindrical tube 12 in a substantially fluid-tight manner. Separating element 18 is generally shaped so as to create, together with the interior surface of cylindrical tube 12, annular passage 26.

Cylindrical tube 12 is substantially circular in cross-section and of substantially constant inside diameter along a major portion of its length. Cylindrical tube 12 is made of a substantially clear and rigid plastic such as Selar polyamide which is manufactured by E. I. Du Pont de Nemours and Company of Wilmington Delaware U.S.A.. Other transparent materials such as high-impact polystyrene, PET, polycarbonate, or glass may be used.

First closure 14 and second closure 16 are similar to stoppers of blood collection tubes known in the art. The portion of first closure 14 and second closure 16 which contacts the interior of cylindrical tube 12 so as to create an air-tight seal is generally made of an elastomeric material such as bromobutyl rubber that reseals after being punctured by a needle or a probe. In the preferred embodiment first closure 14 is constructed so as to be suitable for puncture by a blood drawing needle such as those known in the art. Second closure 16 is constructed to be suitable for puncture by a probe such as that described in U.S. Pat. No. 4,828,716 of McEwen et al.. Although first closure 14 and second closure 16 are shaped having flat ends, one or more of the closures may have a different shape.

Separating element 18 consists generally of fluid control element 20 and separator body 28. Separating element 18 divides the space within the cylindrical tube 12 into first chamber 54 and second chamber 56 wherein second chamber 56 may be initially an incipient chamber which becomes second chamber 56 when the separator is moved within cylindrical tube 12. Separator body 28 may be made of a rigid plastic such as polypropylene or polyethylene. Fluid control element 20 is constructed of a substantially rigid plastic such as nylon, HDPE, high-impact polystyrene or polycarbonate. The shape of the separator body 28 is such that annular passage 26 is formed between the interior surface of the cylindrical tube 12 and the separator body. As will be described later, fluid moving from first chamber 54 to second chamber 56 must pass through annular passage 26. Advantageously, when fluid is within annular passage 26 it may be optically monitored through the wall of cylindrical tube 12 from outside the tube.

The present invention may be used for blood collection and separation. The present invention is intended for use in axial centrifugation as described by McEwen et al. in U.S. Pat. No. 4,828,716 and may be used for conventional centrifugation as well. In practice, blood is collected into the present invention in a manner similar to that used for evacuated blood collection tubes known in the art where first closure 14 is analogous to the stopper of a conventional blood collection tube. After blood has been introduced into blood tube 10 the sample may be processed in an axial centrifuge such that a probe pierces second closure 16 and pushes separating element 18 along the tube to accomplish axial centrifugation according to the method of McEwen et al.

Figure 2:
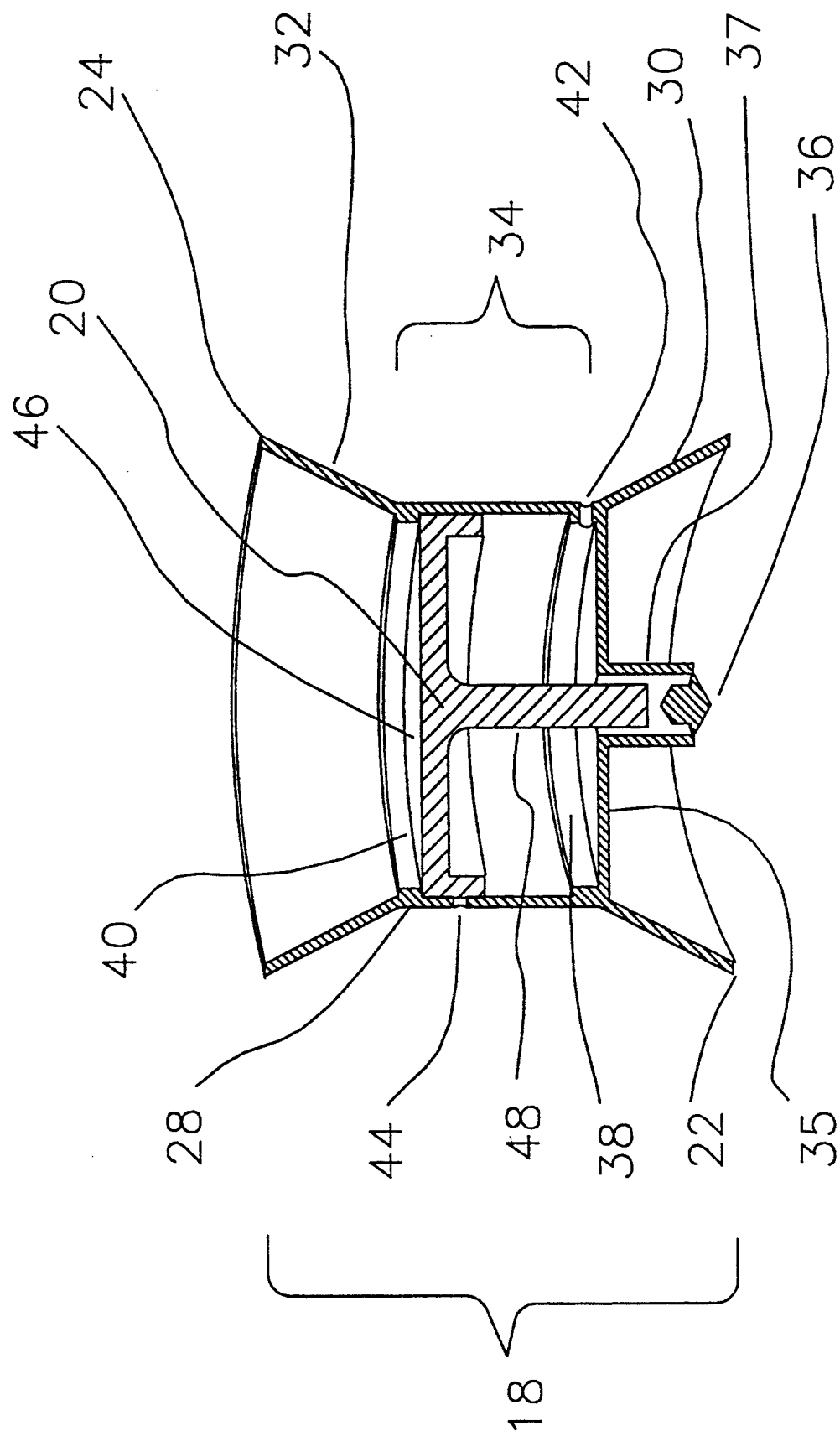
FIG. 2 shows a cross section of the separating element of the preferred embodiment.

FIG. 2 shows separating element 18 in more detail as it appears prior to use. Separating element 18 generally consists of separator body 28 and fluid control element 20.

Separator body 28 consists of first flange 30, second flange 32, waist 34, floor 35, fluid entry channel 37, breakaway tip 36, first valve seat 38, second valve seat 40, first flow-restriction orifice 42, second flow-restriction orifice 44, first wiping seal 22 and second wiping seal 24. Waist 34 is generally shaped as a hollow cylinder and has an outside diameter somewhat smaller than the inside diameter of the cylindrical tube 12 of FIG. 1. First flange 32 is generally frustro-conical in shape with its narrow end joined with a first end of waist 34. Second flange 32 is likewise frustro-conical in shape and is joined at its narrow end to a second end of waist 34. Waist 34, together with first flange 30 and second flange 32 have a general shape corresponding to a hollow cylinder having a diminished diameter toward the middle of its length. Extending across the first end of waist 34 is floor 35 which together with fluid entry channel 37 and break-away tip 36 provide a barrier across the inside diameter of waist 34 that is initially impermeable to fluid. Fluid entry channel 37 is generally a hollow cylinder and is attached substantially in the center of floor 35 by a first end and extends in a direction towards first flange 30 and away from waist 34. Fluid entry channel 37 is terminated at a second end by break-away tip 36. First flange 30, floor 35, fluid entry channel 37 and break-away tip 36 are of one piece and form an initially impermeable fluid barrier when located within cylindrical tube 12 of FIG. 1. Also part of separator body 28 is first valve seat 38 which comprises a circular ring that is one piece with waist 34 and forms a step on the inside diameter of the waist 34 and is located at a first end of the waist 34 that is closest to the floor 35. As will be described, fluid control element 20 moves toward floor 35 to open a fluid passage through fluid entry channel 37. First valve seat 38 restrains fluid control element 20 from moving too far towards floor 35. Second valve seat 40 is similar in construction to first valve seat 38 but is located at a second end of waist 34 that is closest to second flange 32. Also incorporated into separator body 28 is first flow-restriction 42 comprising a small hole which penetrates waist 34 and first valve seat 38 between the exposed flat surface of first valve seat 38 and floor 35. Second flow-restriction orifice likewise comprises a small hole which penetrates the wall of waist 34 and is located diametrically opposite of first flow-restriction orifice 42, but near to second valve seat 40. Separator body 28 is preferably injection molded in one piece of plastic, but may be made of other materials or using other methods of manufacture.

In the preferred embodiment, the space between first flange 30 and second flange 32 is used for optically monitoring the separation process. Although optical monitoring is preferred other methods including visual or ultrasound may be used. When separating element 18 is located within cylindrical tube 12 (FIG. 1), first flange 30 and second flange 32 slidably engage the walls in a substantially fluid-tight manner.

Fluid control element 20 consists of valve 46 and rod 48. Valve 46 is generally disk shaped and is sized so as to slidably fit within waist 34 between first valve seat 38 and second valve seat 40. Valve 46 slidably engages the inside surface of waist 34 in a substantially fluid-tight manner. Rod 48 is substantially cylindrical in shape end extends from the center of valve 46 partway into fluid entry channel 37 toward break-away tip 36. Rod 48 has a diameter somewhat smaller that the interior diameter of fluid entry channel 37 so as to allow the passage of fluid between them.

In practice, separating element 18 is positioned within blood tube 10 (FIG. 1) so that the end of the element containing break-away tip 36 forms part of first chamber 54 into which blood is collected from a patient and forms an impermeable barrier initially preventing blood from flowing through or around the separating element 18.

FIG. 3a and 3b illustrate the separating element as it appears during use showing separating element 18 and probe 50 (arrows show the general direction of fluid flow). FIG. 3b is a view looking along the longitudinal axis of the tube to better describe the fluid flow through the separating element. Within an axial centrifuge similar to the design described in U.S. Pat. Nos. 4,828,716 and 5,030,341 of McEwen et al. a probe 50 is used to move separating element 18 within the blood tube 10 (FIG. 1) to effect separation of the fluid contained in the tube. When probe 50 begins to push on valve 46, separating element 18 resists movement due to a pressure build up in first chamber 54 caused by the lack of a fluid path around or through the separating element. When this pressure build up causes the force exerted through rod 48 on break-away tip 36 to exceed the strength of the joint between break-away tip 36 and fluid entry channel 37, breakaway tip 36 breaks away as shown, valve 46 moves to contact first valve seat 38, and rod 48 clears a path for fluid to flow through fluid entry channel 37. As the separating element 18 continues to move through the fluid, fluid control element 20 constrains the fluid to flow through first flow-restriction orifice 42 into annular passage 26, around waist 34, and through second flow-restriction orifice 44 into enlargening second cheer 56. Advantageously, the convoluted nature of the path through which the fluid must flow impedes fluid flow after the liquid has been separated according to the method of the invention.

In operation, a sample of liquid having phases of different densities such as blood in placed into the blood tube; the operation of the method of the invention will generally be described with reference to separation of blood into a cellular phase and a non-cellular phase. Still Referring to FIG. 3a and FIG. 3b, blood is introduced into first chamber 54. This can be done by removing first closure 14 (FIG. 1) and inserting the blood. However, the blood tube is normally evacuated and can be used to draw blood into first chamber 54 through a cannula pierced through first closure 14 (FIG. 1) as is common in the art.

The present invention is intended for use in an axial centrifuge similar to that described in U.S. Pat. Nos. 4,828,716 and 5,030,341 of McEwen et al. Within an axial centrifuge, the blood tube is rotated at high speed about its longitudinal axis to effect separation of the cellular phase from a lighter, non-cellular phase so that the heavier cellular phases is closest to tube wall 52. Once separation of the phases is substantially complete, probe 50 of the axial centrifuge penetrates second closure 16, engages fluid control element 20, and begins to exert force on the separating element through fluid control element 20. Eventually, the pressure in first chamber 54 increases to the point that break-away tip 36 gives way before rod 48 so that fluid entry channel 37 is opened and fluid begins to flow along the path described by the heavy arrows shown in FIG. 3a and FIG. 3b. Probe 50 continues to exert force on separator 18 moving it along the tube thereby decreasing the volume of first chamber 54. As the volume of first chamber 54 is decreased, the phase that is closest to the longitudinal axis of the blood tube is forced through fluid entry channel 37, through first flow-restriction port 42, though annular passage 26, through second flow-restriction port 44, and into second chamber 56. First, air and non-cellular phase enter annular passage 26 followed by the cellular phase. When cellular phase begins to enter annular passage 26 the cellular phase moves against tube wall 52 and accumulates there obscuring the optical path between tube wall 52 and separator 18 thereby signalling an optical monitoring means which in turn signals probe 50 to stop moving. While the tube is still rotating, the probe is withdrawn from the tube so that it does not come into direct contact with the noncellular phase that is now in second chamber 56. In this way, probe 50 remains uncontaminated so that it can be used on subsequent blood tubes without causing cross-contamination. The rotation of the tube is then stopped and the blood tube is removed from the axial centrifuge. The non-cellular phase may then be removed from second cheer 56 by removing second closure 16 (FIG. 1) and pipetting or pouring the contents. Due to the smallness of the quantity of cellular phase required to signal the optical monitoring means, the convoluted nature of the fluid path, and the small diameters of first flow-restriction orifice 42 and second flow-restriction orifice 44, the cellular phase remains substantially segregated from non-cellular phase (now in second chamber 56). Although adequate under normal circumstances, if the processed tube is handled carelessly or if shipped through the mail or other transport, second flow-restriction orifice 44 may not adequately keep the separated phases isolated. An additional element may be added to the preferred embodiment (FIG. 4) which maintains a more effective post-separation segregation of the phases.

FIG. 4 shows an implementation of the preferred embodiment that includes a spring 60 that returns valve 46 to a position resting against second valve seat 40 so that after a sample of fluid has been separated, the fluid path is closed thereby maintaining isolation of the separated phases of the liquid. When valve 46 is seated against second valve seat 40, second flow-restriction orifice 44 is sealed and the non-cellular phase contained in second chamber 56 (FIG. 3a) segregated from the cellular phases in annular passage 26 (FIG. 3a and FIG. 3b).

Another embodiment of the present invention is shown in FIG. 5a and FIG. 5b. Filter 62 is formed on the exterior flat surface of valve 46 and includes top seal 64. Filter 62 is generally circular and disk shaped having a diameter somewhat less than the inside diameter of second valve seat 40. Valve 46 is formed on a first surface of filter 62 by the process of "insert molding" or some other manufacturing process. Top seal 64 is likewise formed on a second and opposing surface of filter 62 by insert molding or other process. Although shown in a simplified form, features may be formed in filter 62, top seal 64, and/or valve 46 so as to securely fasten them together. Filter 62 is made from a porous material such as Porex TM manufactured by Porex Technologies of Fairburn, Ga., U.S.A.. In use, when separating element 18 is moved according to the method previously described, Filter 62, Valve 46, and top seal 64 are pushed and snapped past second valve seat 40. Top seal 64 seals against the body of separator 18 so as to constrain fluid flowing through second flow-restriction orifice 44 to flow through filter 62. In this way fibrin and other particulate may be filtered from the non-cellular phase. Advantageously, filter 62 further prevents cellular phase from remixing with non-cellular phase after separation has been completed.

I claim:

1. A method of partitioning a pre-selected phase of a sample of liquid having a plurality of phases of differing densities, comprising the steps of:
    (a) introducing said sample of liquid through a first end of a tube and into a first chamber of said tube, said first chamber being separated from a second chamber located at a second opposed end of said tube by a separating element, said second chamber being initially free of the liquid, said separating element slidably engaging the interior surface of the tube in an essentially fluid-tight manner and having a valved flow-restriction orifice therein to permit fluid flow communication between the first and second chambers;
    (b) ordering the phases of the sample within the tube and about the long axis of the tube using axial centrifugation; and
    (c) while the phases are ordered, reducing the volume of the first chamber by movement of the separating element within the tube, and
    (d) moving the valve relative to the orifice such that one phase of the liquid in the first chamber flows through the flow-restriction orifice and into the second chamber as the volume of the first chamber is reduced, said phase in the second chamber being removable therefrom through the second end of the tube.

2. The method of claim 1 in which the second chamber is an incipient chamber that forms as the separating element is moved along the tube.

3. The method of claim 1 wherein a phase of the liquid flows through a passage formed by the separating element and the interior surface of the tube, and said liquid in the passage is externally monitored.

4. The method of claim 1 in which serum or plasma is separated from cellular components of blood.

5. A method of partitioning a pre-selected phase of a sample of liquid having a plurality of phases of differing densities, comprising the steps of:
  (a) introducing said sample of liquid through a first end of a long tube and into a first chamber of said tube, said first chamber being located at the first end of said tube and being separated from a second chamber located at a second opposed end of said tube by a separating element, said second chamber being free of the liquid, said separating element slidably engaging the interior surface of the tube in an essentially fluid-tight manner and having a valved flow-restriction orifice to permit fluid flow communication between the first and second chambers;
  (b) ordering the phases of the sample within the tube about the long axis of the tube; and
  (c) moving the valve toward the first chamber to open the flow-restriction orifice to permit fluid flow communication between the first and second chambers.

* * * * *